(12) United States Patent
Antoine et al.

(10) Patent No.: US 9,999,697 B2
(45) Date of Patent: Jun. 19, 2018

(54) PACKAGING FOR STERILE PRODUCTS

(71) Applicant: DS SMITH PLASTICS FRANCE, Kaysersberg (FR)

(72) Inventors: Jacques Antoine, Stosswihr (FR); Daniel Baumann, Colmar (FR); Jérémy Freneat, Selestat (FR); Christian Maire, Orbey (FR); Sébastien Miranda, Rumersheim le Haut (FR)

(73) Assignee: DS SMITH PLASTICS FRANCE, Kaysersberg (FR)

( * ) Notice: Subject to any disclaimer, the term of this patent is extended or adjusted under 35 U.S.C. 154(b) by 0 days. days.

(21) Appl. No.: 15/312,155

(22) PCT Filed: Feb. 5, 2016

(86) PCT No.: PCT/EP2016/052545
§ 371 (c)(1),
(2) Date: Nov. 17, 2016

(87) PCT Pub. No.: WO2016/124759
PCT Pub. Date: Aug. 11, 2016

(65) Prior Publication Data
US 2017/0072083 A1   Mar. 16, 2017

(30) Foreign Application Priority Data
Feb. 5, 2015  (FR) ...................................... 15 50917

(51) Int. Cl.
*B65D 1/34* (2006.01)
*A61L 2/26* (2006.01)
(Continued)

(52) U.S. Cl.
CPC .................. *A61L 2/26* (2013.01); *A61L 2/206* (2013.01); *A61M 5/002* (2013.01); *B65D 1/34* (2013.01);
(Continued)

(58) Field of Classification Search
CPC ........ A61L 2/26; A61L 2/206; A61L 2202/24; A61L 2202/182; B65D 1/40; B65D 1/34;
(Continued)

(56) References Cited

U.S. PATENT DOCUMENTS 3,481,462 A  *  12/1969  Chapel .................. A61B 50/37
                                                    206/438
3,807,954 A  *  4/1974   McDonald ................ A61L 2/26
                                                    206/210
(Continued)

FOREIGN PATENT DOCUMENTS

FR        2283056 A1      3/1976
WO        2006/095097 A2  9/2006

OTHER PUBLICATIONS

International Search Report dated Mar. 29, 2016, issued in corresponding International Application No. PCT/EP2016/052545, filed Feb. 5, 2016, 2 pages.
(Continued)

*Primary Examiner* — Jacob K Ackun
*Assistant Examiner* — Jenine Pagan
(74) *Attorney, Agent, or Firm* — Christensen O'Connor Johnson Kindness PLLC

(57) ABSTRACT

A packaging for sterile products, comprising a tray and a hood made from cellular plastic material comprising at least two covering sheets held at a distance from one another by a plurality of spacers having cells longitudinally parallel to each other, the tray and the hood comprising a base and sidewalls cut from a plate of said material and with at least
(Continued)

one of said sidewalls having double thickness and being formed by folding two panels of the plate around the folding lines perpendicular to the direction of said spacers. The interior covering sheets are perforated to allow the passage of a sterilizing gas through said covering sheet, the perforations allowing the passage of the gas but preventing the passage of dust, wide cut-outs traversing at least the other covering sheet of the plate in order to ensure communication of said cells with the outside and being provided along the folding lines of said panels.

12 Claims, 2 Drawing Sheets

(51) Int. Cl.
| | |
|---|---|
| *B65D 5/68* | (2006.01) |
| *B65D 5/22* | (2006.01) |
| *B65D 5/42* | (2006.01) |
| *A61L 2/20* | (2006.01) |
| *A61M 5/00* | (2006.01) |
| *B65D 1/40* | (2006.01) |

(52) U.S. Cl.
CPC ................ *B65D 1/40* (2013.01); *B65D 5/22* (2013.01); *B65D 5/4295* (2013.01); *B65D 5/68* (2013.01); *A61L 2202/182* (2013.01); *A61L 2202/24* (2013.01)

(58) Field of Classification Search
CPC .......... B65D 5/68; B65D 5/4295; B65D 5/22; A61M 5/002
USPC .... 206/557, 438, 213.1, 207, 210, 570, 363, 206/370, 439, 484.1; 422/292, 294, 295, 422/297, 300, 26, 28
See application file for complete search history.

(56) References Cited

U.S. PATENT DOCUMENTS

| | | | | |
|---|---|---|---|---|
| 4,550,546 | A * | 11/1985 | Raley | B65B 55/18 |
| | | | | 206/439 |
| 5,518,115 | A * | 5/1996 | Latulippe | B65D 25/10 |
| | | | | 206/370 |
| 5,839,651 | A | 11/1998 | Teags et al. | |
| 6,126,067 | A * | 10/2000 | Grigsby, Jr. | B26F 1/16 |
| | | | | 220/676 |
| 6,808,106 | B1 * | 10/2004 | Grigsby | B65D 5/4295 |
| | | | | 229/120 |
| 8,469,257 | B2 * | 6/2013 | Maillot | A61L 2/206 |
| | | | | 206/213.1 |
| 2010/0264049 | A1 | 10/2010 | Maillot | |

OTHER PUBLICATIONS

Written Opinion of the International Searching Authority dated Mar. 29, 2016, issued in corresponding International Application No. PCT/EP2016/052545, filed Feb. 5, 2016, 5 pages.

* cited by examiner

PACKAGING FOR STERILE PRODUCTS

FIELD OF THE DISCLOSURE

Embodiments of the present disclosure relate to a tray having a cover, both being individually produced by folding and expanding a plate made of semi-rigid plastics material, the tray having the cover being intended to receive sterile products.

BACKGROUND OF THE DISCLOSURE

In order to package and dispatch sterile products, such as medical or surgical instruments or items, for example boxes or sachets containing syringes, it is known to use boxes that are made of cellular plastics material and treated in a sterilisation chamber together with the products that they contain. A known sterilisation treatment method involves filling the box with the not yet sterile product in question as it arrives from manufacturing, then subjecting the whole package to a sterilisation treatment using a suitable gas, such as EtO (ethylene oxide), in a sealed chamber. Following a predetermined exposure time of up to 75 hours, the gas is discharged from the chamber and is replaced with air before the product is removed from the chamber. The treated product is thus dispatched in its box without further handling before it arrives at its destination.

As the gas used for the sterilisation treatment is of a highly toxic nature as it has to eliminate all germs, provision is made to ensure no traces of gas remain trapped inside the packaging. The treatment procedures that are implemented are designed to provide complete safety with respect to the operators and persons responsible for handling the boxes, particularly when leaving the treatment chamber.

Plates of cellular plastics material are readily used for making the packaging boxes. This material is both light and resistant. It is comparable to corrugated cardboard in terms of mechanical performance and has the additional advantage of being durable and more resistant to contamination than said cardboard.

The term "plates made of cellular plastics material" denotes plates consisting of at least two flat parallel sheets that are separated from each other by partitions that are parallel to each other. The sheets and partitions provide longitudinal channels between them, which are called cells in the field. These plates are mainly obtained by extruding a plastics material, such as a polyolefin, through a rectilinear die having a suitable profile, which material is selected depending on the application intended for the material. Immediately downstream of the extrusion head, the material, which is still in the plastic state, passes between calibration plates in order to set the shape of the plate.

This type of plate is now commonly used and can act as a substitute for corrugated cardboard for certain applications, such as the aforementioned application. The common box is the American box. It comprises a strip with four panels each extended on either side by flaps that are folded at a right angle in order to form the base and the top or cover of the box.

The present applicant has developed a box that is used for sterilisation treatment, which box is protected by patent EP 1858760, in which the cover sheets forming the cellular plate are perforated with a plurality of holes to ensure that the gas circulates through said holes during the treatment phase inside the chamber.

SUMMARY OF THE DISCLOSURE

A packaging for sterile products, comprising a tray and a cover made of cellular plastics material comprising at least two cover sheets separated from each other by a plurality of spacers providing longitudinal cells that are parallel to each other, the tray and the cover comprising a base and sidewalls cut from a plate of said material and at least one of said sidewalls being double-layered and formed by folding two panels of the plate around fold lines that are perpendicular to the direction of said spacers, wherein the internal cover sheets are perforated to allow a sterilisation gas to pass through said cover sheet, the perforations allowing the passage of the gas but preventing the passage of dust, wide cut-outs pass through at least the other cover sheet of the plate to ensure that said cells communicate with the exterior, and are provided along the fold lines of said panels.

The packaging has the following additional features that are taken individually or in combination:

The perforations are provided on the sheet of the plate inside the box and the cut-outs are provided on the external sheet.

Openings are made along the fold line between the double wall and the base, said openings being designed to receive locking tabs on the free edge of the external panel and being arranged to allow gas to circulate inside the package from the exterior.

Cut-outs are made along said base fold line, the cut-outs and the openings being arranged in a staggered manner relative to the cut-outs on the line for folding the panels together.

Some of the cells open out onto cut-outs at both ends.

The tray comprises a single double-paneled sidewall.

The walls adjacent to said double sidewall comprise flaps that are arranged between the two panels of the double-paneled wall for holding the walls straight relative to the base.

The cover comprises two double-paneled walls.

The direction of the cells of the cover is perpendicular to that of the cells of the tray.

DESCRIPTION OF THE DRAWINGS

A non-limiting embodiment of the claimed subject matter will be described hereafter in further detail with reference to the accompanying drawings, in which:

DETAILED DESCRIPTION

Figure 1:
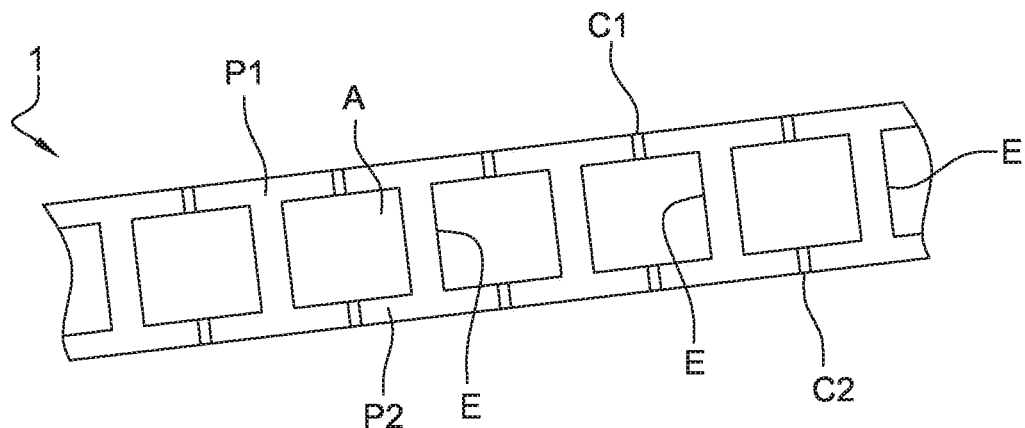
FIG. 1 is a schematic representation of the section of a cellular plate made of cellular plastics material.
Figure 4:
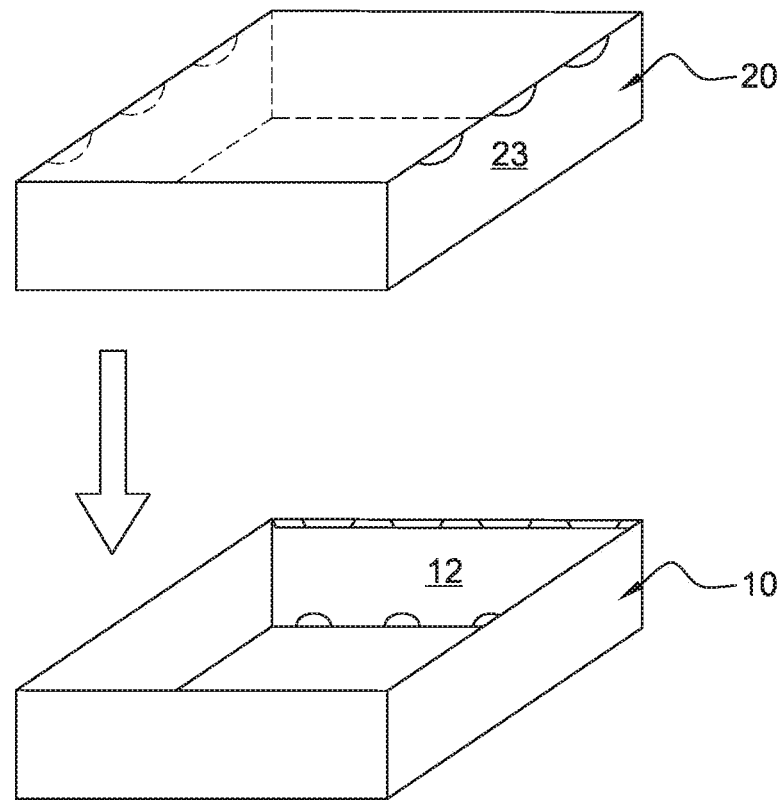
FIG. 4 shows the packaging with the tray and its cover.

FIG. 1 is a sectional view of a plate 1. This plate has two cover sheets P1 and P2. These sheets are connected together by spacers E that are parallel to each other. The space between the cover sheets and the spacers forms longitudinal cells A. In order to make this plate permeable to the gases and impermeable to dust, at least one of the cover sheets, namely the sheet forming the internal wall of the packaging, has been perforated with holes of small diameter. This diameter is defined by experiment. In practice, the diameter of these holes C1 or C2 is between 0.1 and 0.2 mm.

Figure 2:
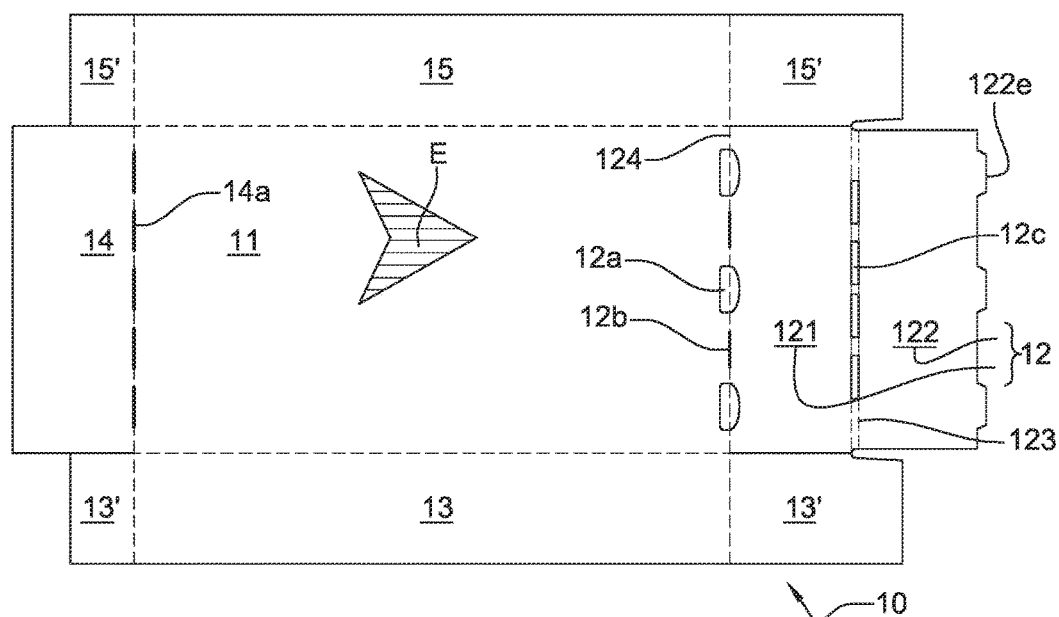
FIG. 2 shows a plate made of cut-out and grooved cellular plastics material that forms a tray following expansion.

FIG. 2 shows a plate that is cut and grooved so as to form the tray of the packaging. The face of the plate inside the tray is perforated with holes C. The external face also can be perforated; preferably, it is not perforated. The grooves are shown using dashed lines and the cut-outs are shown using solid lines. This plate 10 comprises a panel 11, forming the base of the tray, which is demarcated by four fold lines, with side panels forming the sidewalls: 12, 13, 14 and 15 of the tray. The panel 12 that is perpendicular to the direction of the spacers E is a double panel. It is made from two panels: a first panel 121 that is hinged around a fold line 124 of the base panel 11, and a second panel 122 that is hinged around a fold line 123 around the first panel 121. Cut-outs 12c are made along the fold line 123; four cut-outs are shown in FIG. 2. The intention is to not weaken the link between the panels whilst opening as many cells as possible. Openings are also made along the fold line 124. These openings 12a and 12b are arranged in a staggered manner relative to the cut-outs 12c, such that all of the cells communicate with the atmosphere at least via one end. Some 12a of the cut-outs are widened in order to form an inlet/outlet for the gases in the chamber of the packaging.

Tabs 122e are arranged along the free edge of the panel 122, corresponding to the openings 12a. The aim is to lock the panel 122 in position against the panel 121 upon expansion by inserting the tabs into the openings 12a.

In this embodiment, the panel 14 opposite the panel 12 is a single panel. All of the cells are open, but cut-outs 14a are provided along the fold line to vent the cells.

Figure 3:
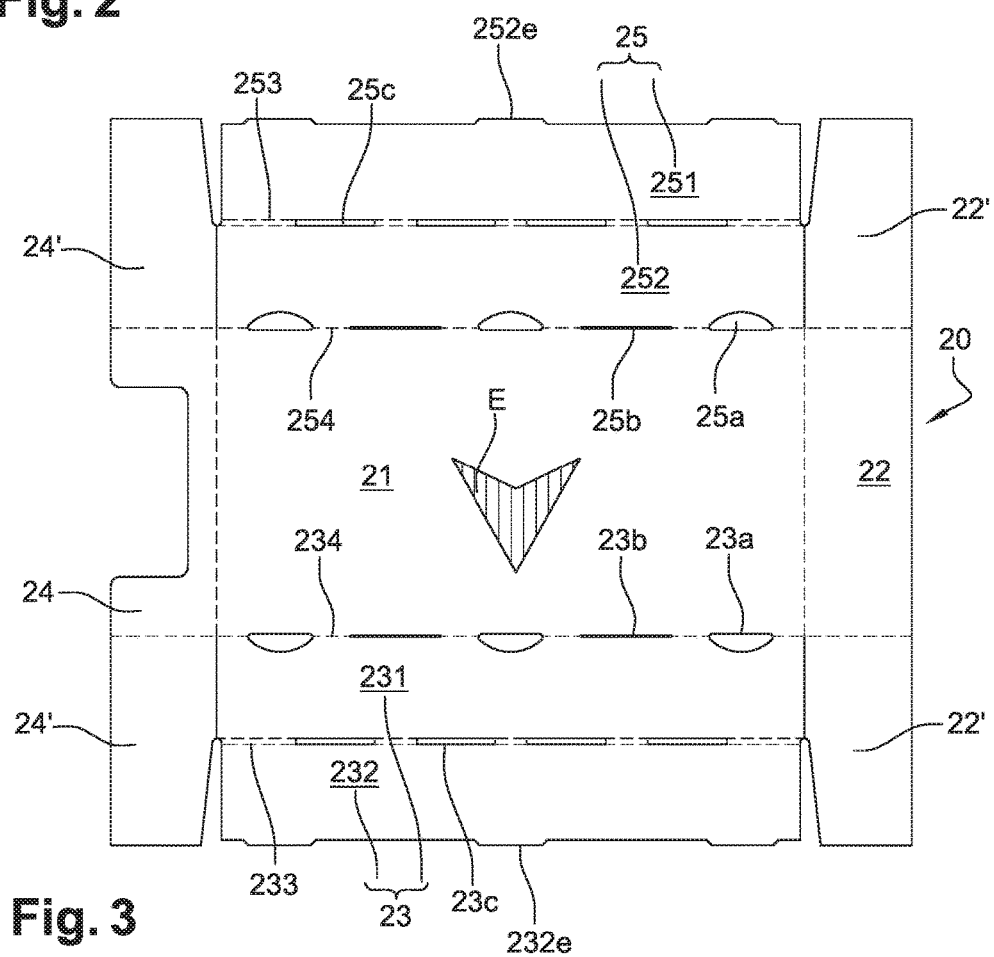
FIG. 3 shows a plate made of cut-out and grooved cellular plastics material that forms a cover following expansion.

FIG. 3 shows a plate 20 that is cut and grooved so as to form the cover of the packaging. The face of the plate that forms the inside of the cover is perforated with holes C; the external face also can be perforated. The grooves are shown using dashed lines and the cut-outs are shown using solid lines.

The panel 21 forming the base of the cover is demarcated by fold lines, with panels forming the sidewalls of the cover: 22, 23, 24 and 25. The panels 23 and 25 in the direction of the spacers E of the plate are double panels: 231, 232 and 251, 252, respectively, that are hinged around fold lines 234 and 254, respectively, on the base panel, and around fold lines 233 and 253, respectively, between each other. Cut-outs are made along fold lines 233 and 253, namely the cut-outs 23c and 25c, respectively. As with the cut-outs 12c, their number and length are a compromise between the strength needed between the panels 231, 232; 251, 252 and the venting of the cells into the atmosphere.

Similarly, cut-outs 23b, 25b, respectively, and openings 23a, 25a, respectively, are made along fold lines 234 and 254, respectively, in a staggered manner with respect to the cut-outs 23c, 25c, respectively. The openings 23a and 25a have the same functions as the openings 12a in the tray.

The panels 22 and 24 are extended by flaps 22' and 24' that are arranged so as to be able to be housed between the panels of the walls 23 and 25 upon expansion.

With respect to the expansion of the tray and the cover, the side panels are arranged at a right angle to the respective base panel and the flaps are placed against the first panels 121, 231 and 251 of the double walls. The second panels are then folded over the flaps and the tabs 122e, 232e and 252e are inserted in the corresponding openings.

In this embodiment, the wall 14 is a single wall in order to allow the tray to be loaded via this side, the panel being flat.

Once the products are placed in the tray, the cover is fitted and the entire package is ready for sterilisation. As a priority, the gas enters via the openings 12a, 23a and 25a. Conversely, after sterilisation the gas is mainly exchanged via the openings, but the cut-outs also allow rapid exchange of gas in the cells of the plate by virtue of the cut-outs.

The direction of the cells is perpendicular to the hinge lines of the double panels. The direction could form an angle other than a right angle, but it is not parallel to said lines.

The cut-outs can be simple slots made with a blade through one or both of the cover sheets. They also can be made such that the cut-out edges are spaced apart from each other. The spacing can be several millimeters.

According to a further embodiment (not shown) slits are made in the external sheet of the panels of the box. These slits are narrow and extend through a plurality of cells.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. Packaging for sterile products, comprising:
   a tray and a cover made of cellular plastics material comprising at least two cover sheets separated from each other by a plurality of spacers providing longitudinal cells that are parallel to each other, the tray and the cover comprising a base and sidewalls cut from a plate of said material and at least one of said sidewalls being double-layered and formed by folding two panels of the plate around fold lines that are perpendicular to the direction of said spacers, wherein
   the cover sheet positioned inside the packaging is perforated by perforations to allow a sterilisation gas to pass through said cover sheet, the perforations allowing the passage of the gas but preventing the passage of dust, and wherein
   wide cut-outs pass through at least the other cover sheet of the plate to ensure that said cells communicate with the exterior, and are provided along the fold lines of said panels.

2. Packaging according to claim 1, wherein the perforations are made on the sheet of the plate inside the box and the cut-outs are made on the external sheet.

3. Packaging according to claim 1, wherein openings are made along the fold line between the double wall and the base, said openings being designed to receive locking tabs on a free edge of the external panel and being arranged to allow gas to circulate inside the packaging from the exterior.

4. Packaging according to claim 3, wherein cut-outs are made along said base fold line, the cut-outs and the openings being arranged in a staggered manner relative to the cut-outs on the line for folding the panels together.

5. Packaging according to claim 4, wherein some of the cells open onto cut-outs at both ends.

6. Packaging according to claim 1, wherein the tray comprises a single double-paneled sidewall.

7. Packaging according to claim 1, wherein the walls adjacent to said double sidewall comprise flaps arranged between the two panels of the double-paneled wall for holding the walls straight relative to the base.

8. Packaging according to claim 1, wherein the cover comprises two double-paneled walls.

9. Packaging according to claim 8, wherein the direction of the cells of the cover is perpendicular to that of the cells of the tray.

10. A component of a sterile product packaging, comprising:
   a base and sidewalls formed of a cellular plastics material structure, said cellular plastics material structure comprising an interior cover sheet and an exterior cover sheet separated from each other by a plurality of spacers providing longitudinal cells that are parallel to each other, at least one of said sidewalls being double-layered and formed by folding two panels of the cellular plastics material structure around fold lines that are not parallel to the direction of said spacers,
   wherein the interior cover sheet is perforated by perforations to allow a sterilization gas to pass through said interior cover sheet, the perforations allowing the passage of the gas but preventing the passage of dust, and
   wherein wide cut-outs pass through at least the exterior cover sheet to ensure that said cells communicate with the exterior, and are provided along the fold lines of said panels.

11. The component of claim 10, wherein the component is a tray.

12. The component of claim 10, wherein the component is a cover.

* * * * *